(12) United States Patent
Weinstock (10) Patent No.: US 8,849,371 B2
(45) Date of Patent: *Sep. 30, 2014

(54) SYSTEM FOR ANALYZING AND TREATING ABNORMALITY OF HUMAN AND ANIMAL TISSUES

(71) Applicant: NewLife Sciences LLC, Merrimack, NH (US)

(72) Inventor: Ronald J. Weinstock, Corona Del Mar, CA (US)

(73) Assignee: NewLife Sciences, LLC, Merrimack, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/690,752

(22) Filed: Nov. 30, 2012

(65) Prior Publication Data

US 2013/0317565 A1    Nov. 28, 2013

Related U.S. Application Data

(63) Continuation of application No. 13/269,017, filed on Oct. 7, 2011, now Pat. No. 8,326,398, which is a continuation of application No. 12/456,657, filed on Jun. 19, 2009, now Pat. No. 8,064,988, which is a continuation of application No. 10/856,632, filed on May 28, 2004, now Pat. No. 7,801,585.

(60) Provisional application No. 60/474,843, filed on Jun. 2, 2003.

(51) Int. Cl.
*A61B 5/05*    (2006.01)
(52) U.S. Cl.
USPC ........... 600/407; 600/411; 600/427; 600/439; 600/431; 601/2; 606/32; 606/33
(58) Field of Classification Search
USPC ......... 600/407, 410, 431, 506, 411, 427, 439; 601/2
See application file for complete search history.

(56) References Cited

U.S. PATENT DOCUMENTS 8,326,398 B2 *    12/2012    Weinstock .................... 600/407

* cited by examiner

*Primary Examiner* — James Kish
*Assistant Examiner* — Joel Lamprecht
(74) *Attorney, Agent, or Firm* — Nixon Peabody LLP (57) ABSTRACT

A patient treatment unit for analyzing and treating abnormality of human or animal tissues, includes a display; a pulse generator circuit that outputs a sequence of electrical pulses at a pulse frequency, the electrical pulses having a pulse width, the pulse generator controlling the pulse frequency and the pulse width of the electrical pulses; a pair of probes for contacting a body of a patient and electrically coupled to the pulse generator; and a voltage and current sensing circuit that senses a voltage or a current via the probes when contacting the body of the patient.

9 Claims, 12 Drawing Sheets

OUTPUT WAVEFORM

MAXIMUM INTENSITY AND FREQUENCY

FIG.5A  1-M-Ohm IMPENDANCE

OUTPUT- 500 Ohm IMPEDANCE-POWER: MAXIMUM-
FREQUENCY: MAXIMUM

FIG.5B

OUTPUT - 5K Ohm IMPEDANCE - POWER: MAXIMUM - FREQUENCY: MAXIMUM

FIG. 5C

OUTPUT - 10K Ohm IMPEDANCE - POWER: MAXIMUM FREQUENCY: MAXIMUM

SYSTEM FOR ANALYZING AND TREATING ABNORMALITY OF HUMAN AND ANIMAL TISSUES

REFERENCE TO RELATED APPLICATIONS

The present application is a continuation of U.S. application Ser. No. 13/269,017, filed Oct. 7, 2011, (now U.S. Pat. No. 8,326,398), which is a continuation of U.S. application Ser. No. 12/456,657, filed Jun. 19, 2009, (now U.S. Pat. No. 8,064,988), which is a continuation of U.S. application Ser. No. 10/856,632, filed May 28, 2004, (now U.S. Pat. No. 7,801,585), which claims the benefit under 35 USC 119(e) of the provisional patent application Ser. No. 60/474,843, filed Jun. 2, 2003. All prior applications above are hereby incorporated by reference in their entirety.

BACKGROUND OF THE INVENTION

A. Area of Invention

The present invention relates to electromedicine and, more particularly, to the application of a magnetic field to tissue and the subsequent measurement of electron spin and paramagnetic resonance properties of the tissue to ascertain and treat abnormalities associated therewith and with specific disease states.

B. Prior Art

The value and application of electron magnetic resonance (EMR) in biomedicine has been recognized, given its similarity, at least in principle, to proton magnetic resonance (often termed nuclear magnetic resonance or NMR). However, the field and frequency conditions under which an EMR signal is seen are different. In proton MRI, one of most common forms of NMR, the DC field may be on the order of 20,000 gauss (2 Tesla) at a radio frequency of about 85 MHz. In new high resolution NMR, the field strength may be increased to 12 Tesla at a microwave frequency of about 500 MHz. In distinction, the field associated with an EMR field may be as low as a fraction of a Tesla and under 1 GHz. These conditions, which historically related to different instrumentation, more importantly have lead to the realization that EMR techniques can be several orders of magnitude more sensitive than NMR, given that the electron magnetic moment is approximately 650 times stronger than that of the proton, even though the mass of the electron is far less than that of a proton, as above noted, is obtainable at field strengths and frequencies that are far less intrusive and, thereby, less hazardous than those associated with NMR. Because of these actors, the primary historic use of the NMR has been in association with analysis, imaging, and diagnosis of a wide variety of tissue related traditions, while NMR found little application in the treatment of tissue abnormalities or disorders.

EMR was discovered in 1925 by Goudsmit and Uhlenbeck. Thereafter its practical application was primarily in EMR spectrometers and, through the present, is used primarily in such applications. See for example U.S. Pat. No. 6,335,625 (2002) to Bryant et al.

EMR, sometimes termed electron paramagnetic resonance (EPR), has become a generic name given to the magnetic behavior of the electron when immersed in an external magnetic field. In EMR, the electron exhibits two key properties, namely, its magnetic field and a gyroscopic behavior. Therein, its electric field plays no part. Its magnetic field is often termed its dipole moment while its gyroscopic behavior is called its gyroscopic moment.

The greater the time domain differences between the magnetic components of an electromagnetic wave of a tissue, the greater will be the phase differences between the components and, thereby, the greater the energy loss or gain. As such, measurement of differences in phase between both magnetic moments of the electron have developed as a means of recognizing differences of properties between respective materials subject to an EM wave of typically of dipole and gyroscopic moment inducing strength. This phase change and energy loss or gain relates exponentially to cellular and tissue function.

From the perspective of quantum mechanics, the electron, while shifting positions within a permissible set of patterns relative to the atomic nucleus, generates specific energy emissions or spectra, i.e., EMR by body tissues and physiological structures. Such patterns have been found to comprise unique tissue signatures and, as such, a product of the individual atomic, molecular and cellular quantum movements which characterize the given tissue, organ or physiological structure of interest. Thereby, from my perspective of biophysics, the initial step in pathology emanating from a dysfunctional, damaged or diseased tissue is considered a misfunction of the EMR of the normal electron cloud associated with such tissue. EMR disorders thereby predispose biochemical and bio-electrical alterations reflected in each unique EMR signature of the tissue or structure of interest. When a disorder of measurable EMR occurs, the resonance and configuration of the normal electron cloud at the atomic level exhibit phase shifts which break and disturbs the otherwise orderly pathways of communication from atom to molecule, molecule to cell, cell to tissue, and tissue to organ. This results in breakdown in molecular and cellular communication one end result for example being a reduction in tissue conductivity.

For the inventive electron magnetic resonance analyzer and treatment system to function, the system sends or receives information to and from the body, the body's cellular network or in some cases, the central nervous system, that is, its pain processing center. This pathway allows the EMR of the inventive system to record and analyze any phase-shifted EMR patterns emanating by and from the body's tissues and structures.

In case of assessing and treating pain, the inventive system also employs inductors and applicators at the site of pain, tissue abnormality and/or upon selected nervous system trigger or motor points (which can also comprise of acupuncture or pressure points). A synthesized EMR pattern is transmitted into the tissue which encounters the inherent resonance pattern produced by the tissue or subject matter under study. The information generated by this initial step of the analysis process is returned to the system where, after removal of impedance static in the signal it is analyzed, digitized and, if desired, compared to predetermined EMR patterns associated with such normal tissue. Thereby, the recorded data is assessed and evaluated for irregulates or abnormalities. The inherent EMR signatures of normal atoms, molecules, tissues and structures may thereby be employed as "standards" in the digitizing of values based on recorded and peak resonance emissions of healthy, non-diseased, non-damaged tissues. When such a first phase of the EMR pattern measurement and assessment is complete, the system has detected any disorder or shifting of EMR peaks at the pain site under study, if a phase shifts exists.

A second aspect of operation of the inventive system is that of its therapeutic action. If an EMR phase shift of the targeted tissue or organ is detected in the first aspect of analysis, the shift can be corrected through the application of a counter or neutralizing EMR which, as set forth below, is calculated and computed by the system, thereby resulting in a neurotransmitter function which is regulated by administration of a counter EMR pattern. It has been found that upon realignment of the phase shifted EMR pattern, reduction and alleviation of pain occur instantaneously, healing time is reduced and, upon suitable repetition of therapy, result in long term improvement of the abnormality of interest.

Pain is reduced or eliminated by means of effect on nociceptive afferent neurons which are sensitive to magnetic as well as a variety of noxious stimuli including thermal, mechanical, and chemical. Excitation of nociceptive neurons induce a field gradient into magnetic sensitive ion channels, particularly sodium, calcium and potassium channels. Nerve terminal membranes are magnetically encoded through the activation of inward depolarizing membrane currents or activation of outward currents. The main channels responsible for inward membrane currents are the voltage activated sodium and calcium channels.

It is known that an ionic gradient exists across the plasma membrane of virtually all human and animal cells. In particular, the concentration of potassium ions inside the cell is about ten times that in the extracellular fluid. Also sodium ions are present in much higher concentrations outside a cell than inside. As such, the potassium and sodium channels play an important role in membrane excitation and, thereby, in determining the intensity of pain. Sodium channels are now considered a destabilizing membrane in the pain process. These channels, which can open rapidly and transiently when the membrane is depolarized beyond about minus 40 mV, are essential for action of most neurons, potential generation, and conduction. These open channels are also believed to be responsible for the neuron action leading to pain. Sodium is also an alkali element (with an atomic number of 11) and is paramagnetic. That is, when placed in a magnetic field, a paramagnetic substance becomes magnetized parallel to the field. It is believed that a magnetic interaction thereby occurs between sodium channels and the EMR patterns and peaks discussed above. EMR affects sodium which in turn affects the excitability of nociceptive neurons which are chemically distinct from most other neurons It has been found that EMR fields which consist of an EM carrier of a range of about 1 Hz to about 1 GHz, when modulated by EMR patterns in a range of about 0.1 gauss to about 4 Tesla, provide a regulating effect upon sodium channels, this leading to pain reduction.

Tests have also indicated that EMR fields alter the pH level of water, which relates to another theory of the pain reduction associated with the present system. That is, it has been shown that the pH of extra-cellular fluid is associated with a number of patho-physiological conditions such as hypoxia/anoxia and inflammation. It has been reported that the pH of synovial fluid from enflamed joints is significantly more acid than is that of normal joints. As such, low pH solutions evoke a prolonged activation of sensory nerves and produce a sharp stinging pain. Consequently, when pH of tissue is changed, pain reduction is often achieved.

Successful treatment of arthritis, fibromyalgia, neuralgia, neuropathy, categories of joint and tissue injury, wound healing, calcific tendonitis, and various types of migraine headaches has been demonstrated.

SUMMARY OF THE INVENTION

A patient treatment unit for analyzing and treating abnormality of human or animal tissues, includes a display; a pulse generator circuit that outputs a sequence of electrical pulses at a pulse frequency, the electrical pulses having a pulse width, the pulse generator controlling the pulse frequency and the pulse width of the electrical pulses; a pair of probes for contacting a body of a patient and electrically coupled to the pulse generator; and a voltage and current sensing circuit that senses a voltage or a current via the probes when contacting the body of the patient.

It is an object of the present invention to employ principles of electron magnetic resonance (EMR) for the analysis and relief of pain and correction of abnormalities of human tissue.

It is another object to provide a system to analyze and digitize normal EMR patterns of specific tissues.

It is further object of the invention to correct abnormal EMR patterns by applying a countervailing or neutralizing EMR field spectra utilizing inductive sensors and applicators to apply EMR patterns of an intensity from about 0.1 gauss to about 4 Tesla.

It is further object to measure and analyze EMR out-of-phase peak resonances associated with abnormal tissue function, chronic pain, and traumatic injuries of soft tissue.

It is further object to provide a system of the above type in which useful. EMR pattern information is measured at a trigger point, at or near a tissue dysfunction or pain site, and a counter resonance pattern is applied to said site to realign phase shifted resonance patterns associated with the electron of cells affection by an abnormal or pain condition.

It is further object to provide a system of the above type which can be readily interfaced with existing electromedical technologies including, without limitation, CT Scan, MRI, stereotactic imaging, and PET scanning. The advantage of this interface is the ability to visually "light up" an anatomical area with phase shift activity. By using an algorithm to monitor the amplitude of the signal and the degree of electromagnetic flux variation, various colors can be assigned to this phenomenon indicating antiphase or phase shifted areas. i.e., red being a reactive area and blue being a normal area. This information can then overlay a two or three dimensional diagnostic image, visually pinpointing an antiphase or phase shifted anatomical area. The advantage of this is being able to visualize functional variations and abnormalities as well as gross anatomical abnormalities. Another iteration of the technology is the attachment of an LCD screen to the back of a hand held wireless induction coil. Anatomical areas of the body can be scanned while watching for color changes on the attached LCD when a phase shift area is detected.

The above and other objects in advantage of the present invention will become apparent from the hereinafter set forth. Brief Description of the Drawings, Detailed Description of the Invention and Claims appended herewith.

DETAILED DESCRIPTION OF THE INVENTION

Figure 1:
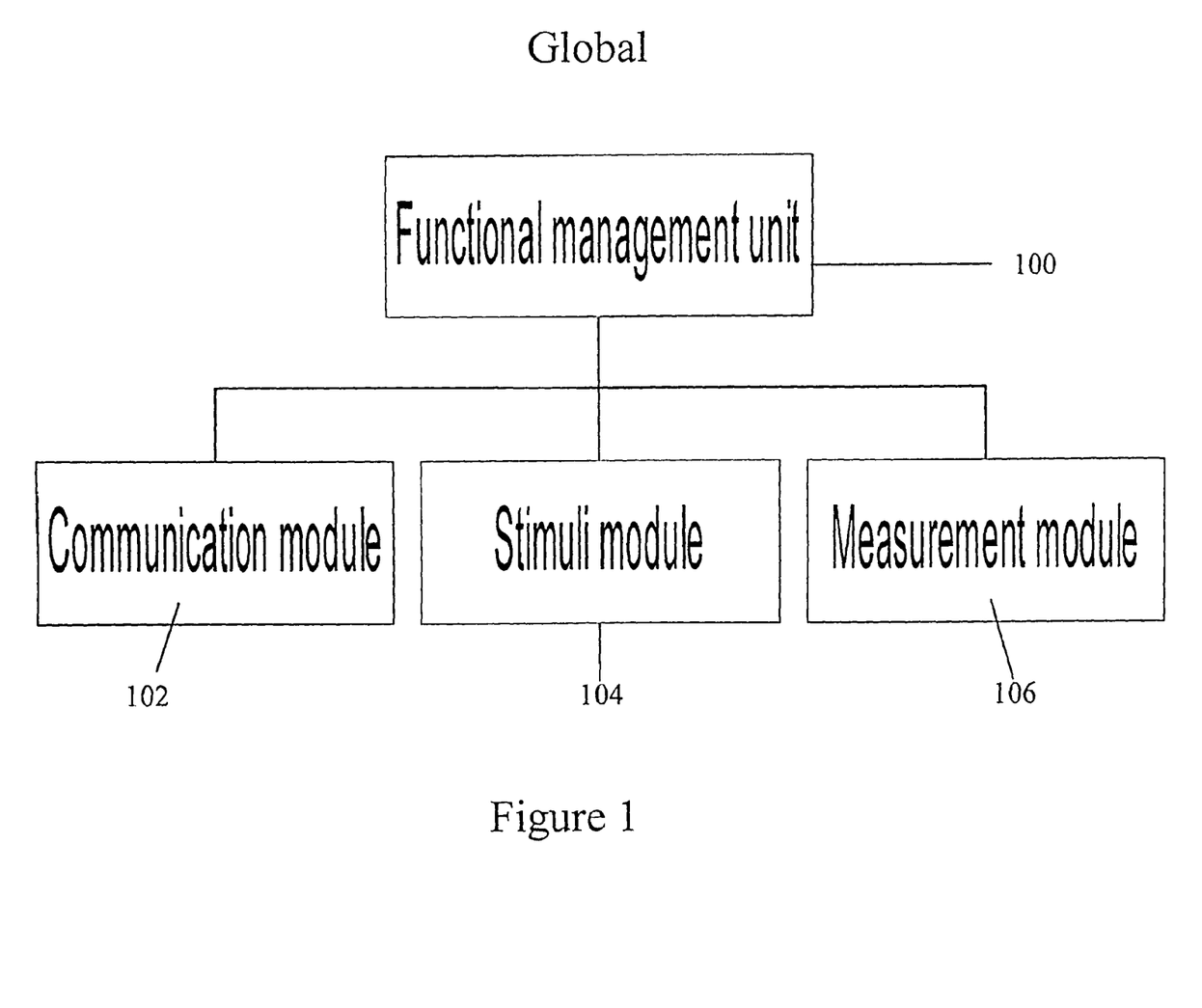
FIG. 1 is a block diagram showing the basic hardware and software functions of the inventive system.

With reference to the general block diagram view of FIG. 1, my inventive system for analyzing and treating abnormality of human and animal tissues may be seen to include a functional management unit ("FMU") 100 which supervises functions of a communication module 102, a stimuli module 104, and a measurement module 106.

Figure 2:
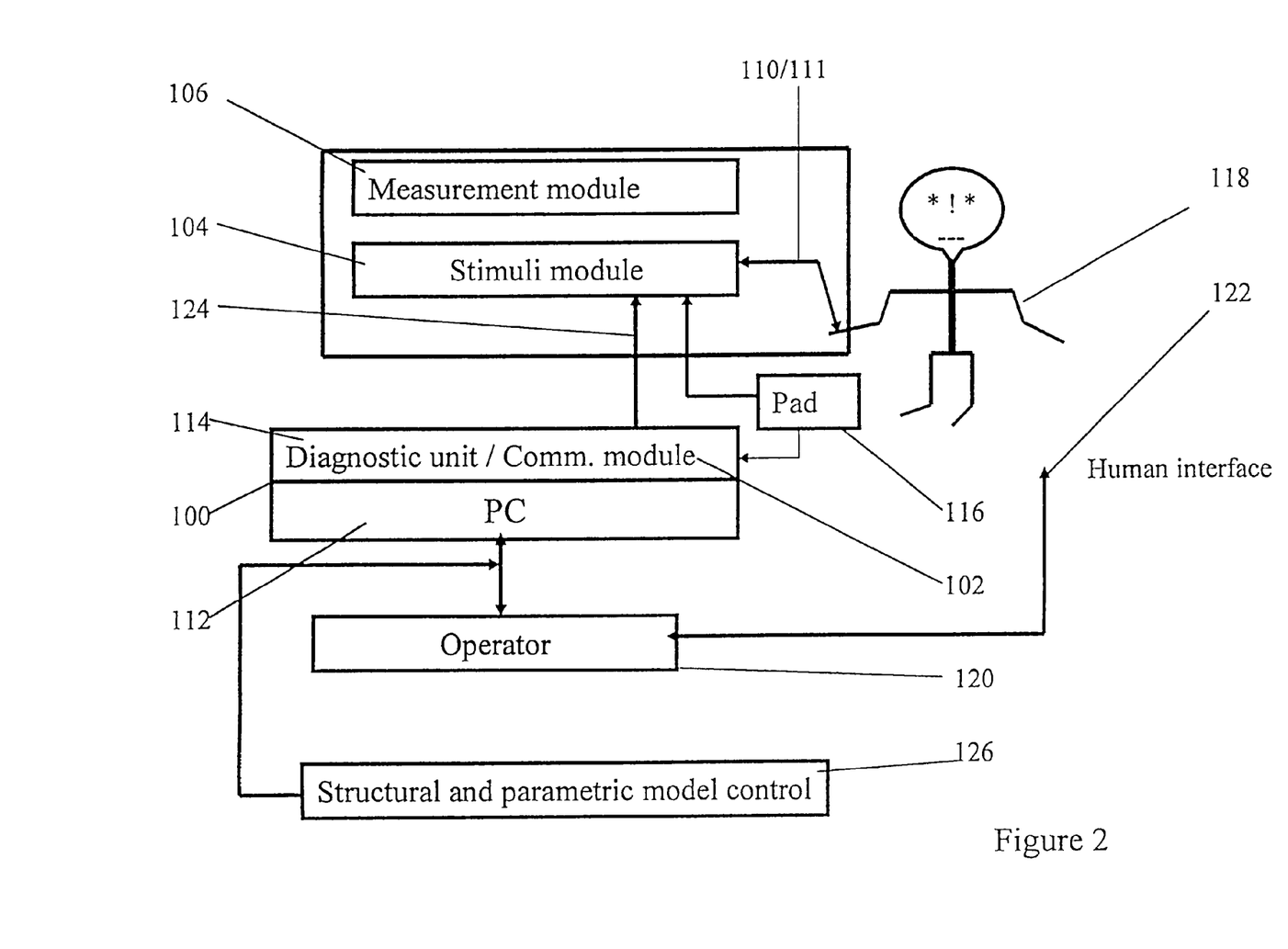
FIG. 2 is a schematic view of a patient treatment unit ("PTU") and associated diagnostic unit.

As may be noted in FIG. 2, the primary hardware of the inventive system is associated with a patient treatment unit ("PTU") 108 which includes said measurement module 106 and stimuli module 104. The stimuli module functions through probes or induction coils 110/111 thru which the initial data required by measurement module 106 is captured. In FIG. 2 may also been seen the physical relationship between a PC 112 and a diagnostic unit 114 which includes said communication module 102. Diagnostic unit 114 and PC 112 comprise integral components of said FMU 100. Further shown in FIG. 2 are pads 116 which facilitate treatment of patient 118 by an operator 120. Line 122 represents a human and animal interface between patient 118 and operator 120 while line 124 represents a radio interface means between the PC and diagnostic unit, 114 on the one hand, and the PTU 108 on the other. Structural and parametric heuristic control of diagnostic unit 114 and PTU 108 are indicated by line 126 of FIG. 2.

The electrical output specifications of PTU 108 are as follows:

| | |
|---|---|
| Power Supply | 115 VAC, 60 Hz |
| Maximum Power Consumption | 21 W |
| Output voltage | Range of normal use: 50-60 V |
| | Peak pulse amplitude: 120 V |
| Pulse Rate | 1-490 Pulses/second, ±6% |
| Pulse Duration | 0.34-0.74 millisecond |
| Output Current (maximum) | 8.9 milliamps |
| Maximum charge per pulse | 7 micro coulombs |
| Wave Form | Complex pulse trains: variable frequency, variable pulse width, AC-coupled rectangular pulse |

Figure 3:
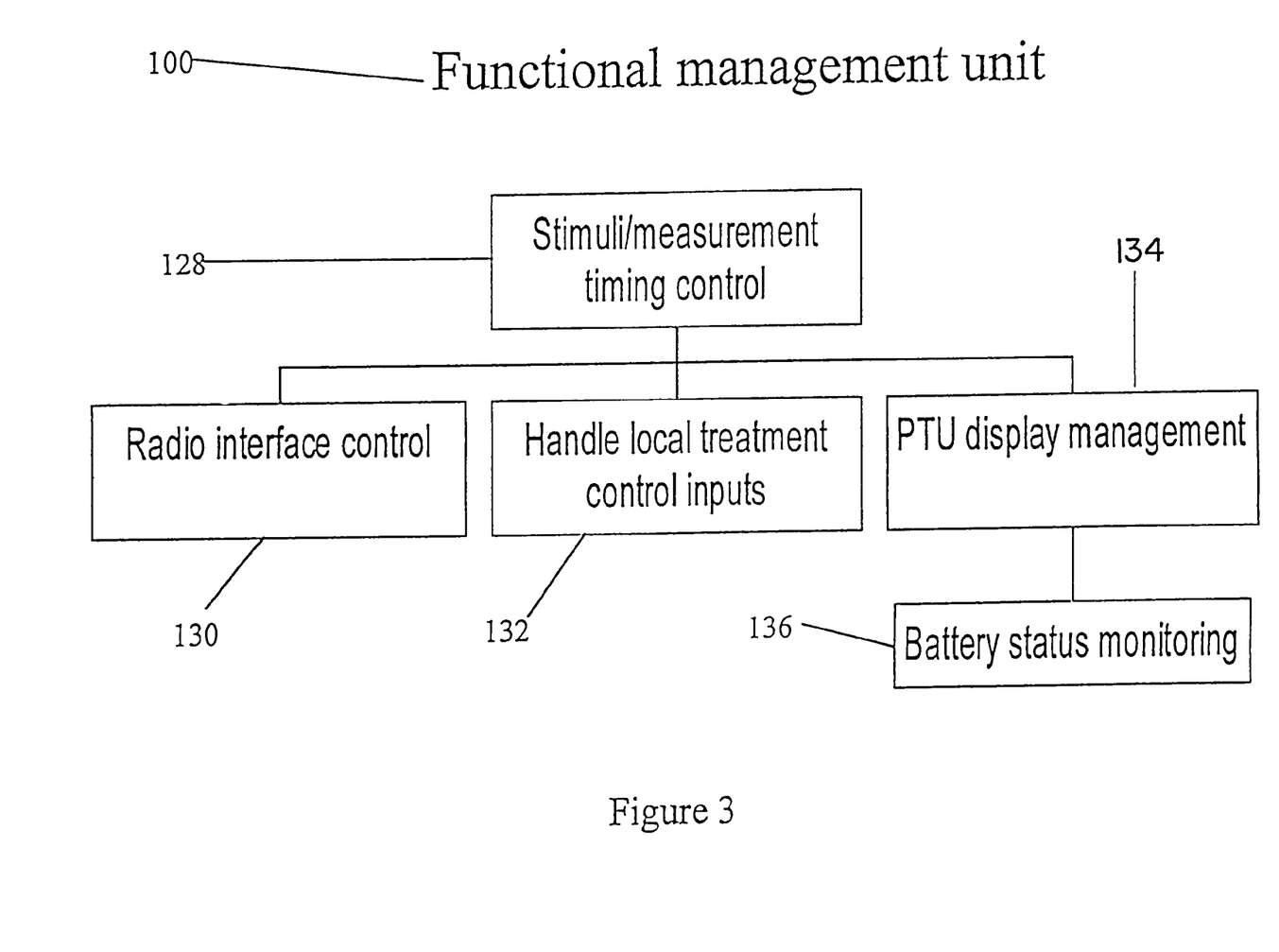
FIG. 3 is a block diagram view of a functional management unit ("FMU").

In FIG. 3 is shown FMU 100, inclusive of stimuli-measurement timing control means 128, radio interface control 130, local handle treatment control inputs 132 which are associated with said pads 116, a PTU display management facility 134 associated with said diagnostic unit 114, and a battery status monitor 136.

Figure 4:
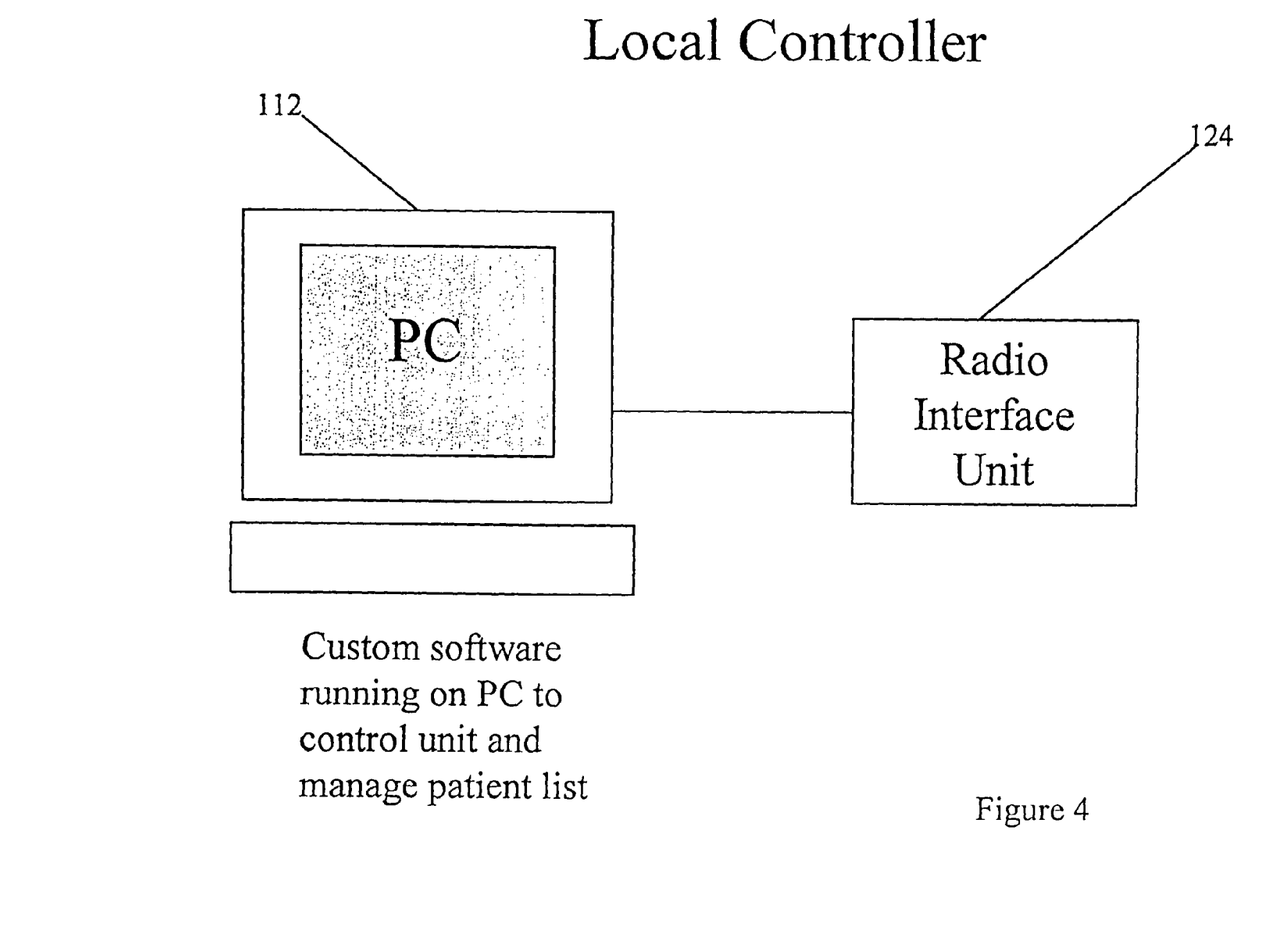
FIG. 4 is a block diagram view of the local controller and system custom software operating upon a PC platform to control the PTU and manage a patient list. Also shown is a radio interface unit between the PC and the PTU.

In FIG. 4 is schematically shown the use of custom software running upon said PC 112 to control the PTU 108 and manage a patient list. Said PC is connected to a PTU 108 through said radio interface 124.

Figure 5:
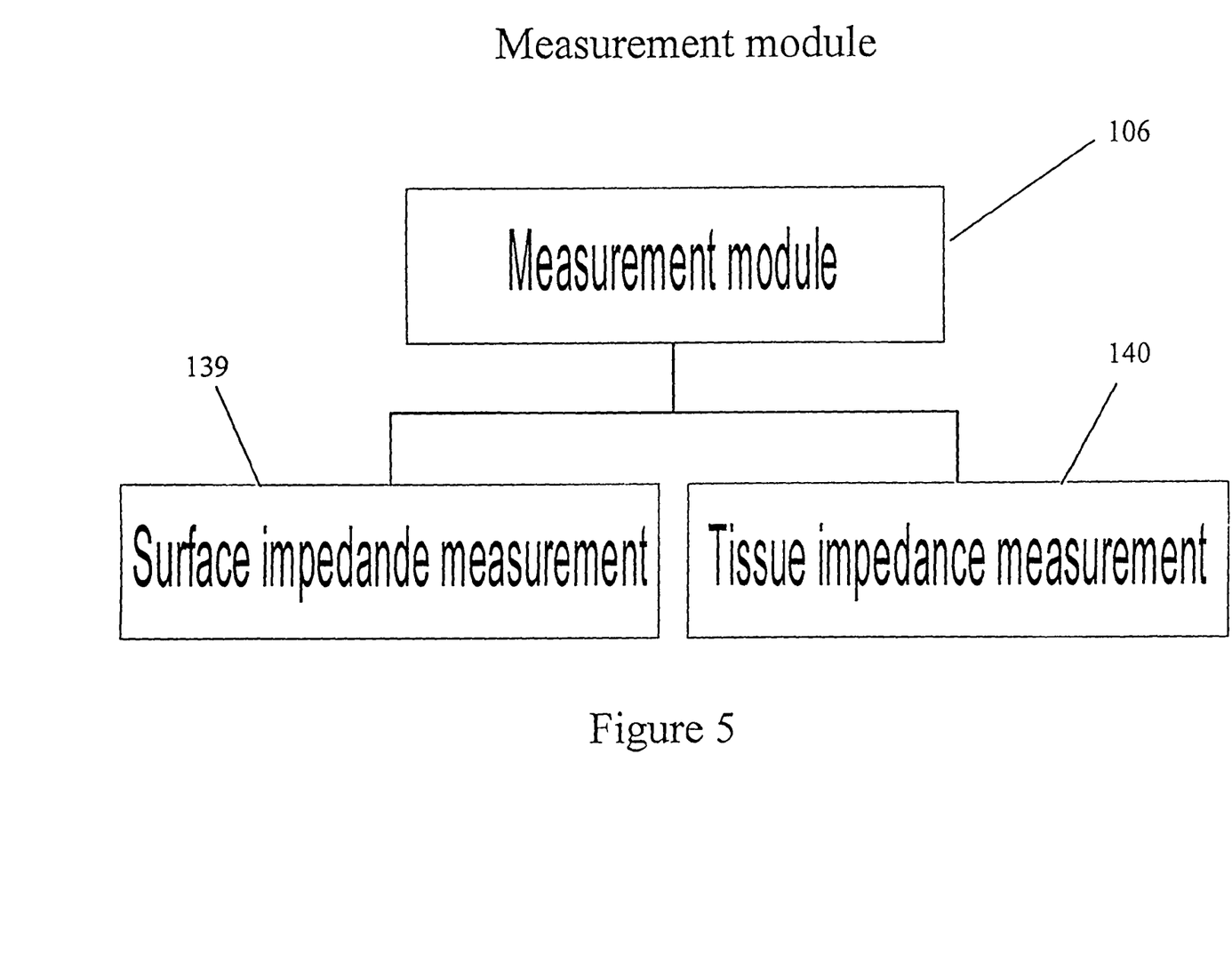
FIG. 5 is a block diagram view of a tissue measurement module.
Figure 5A:
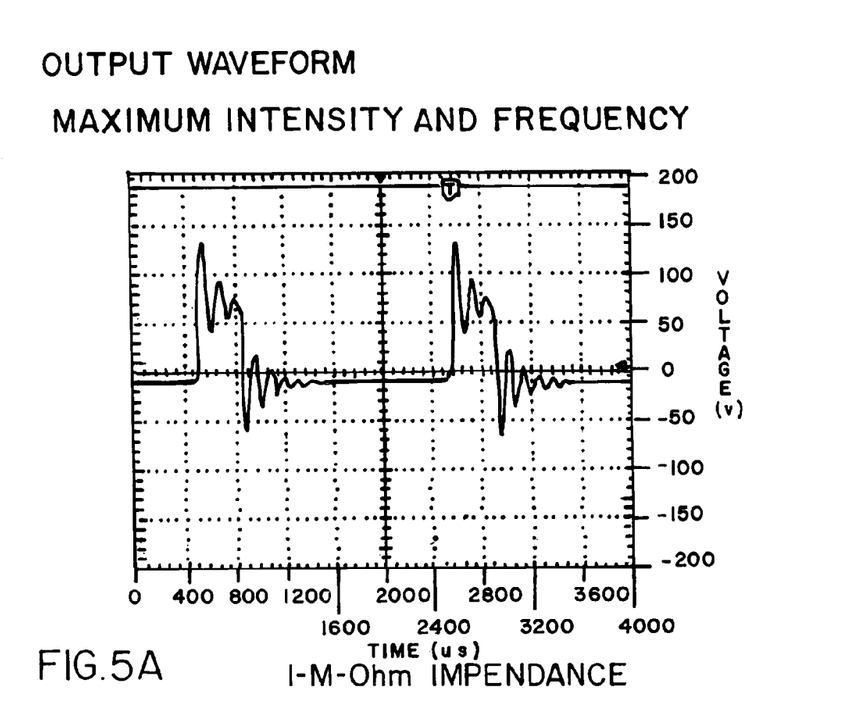
FIGS. 5A-5D show impedance, power and frequency relationships for the PTU.

In FIG. 5 is shown measurement module 106 which includes means 138 for measurements of the surface impedance of a treated tissue and means 140 for measurement of the impedance of the tissue to be treated.

Figure 5B:
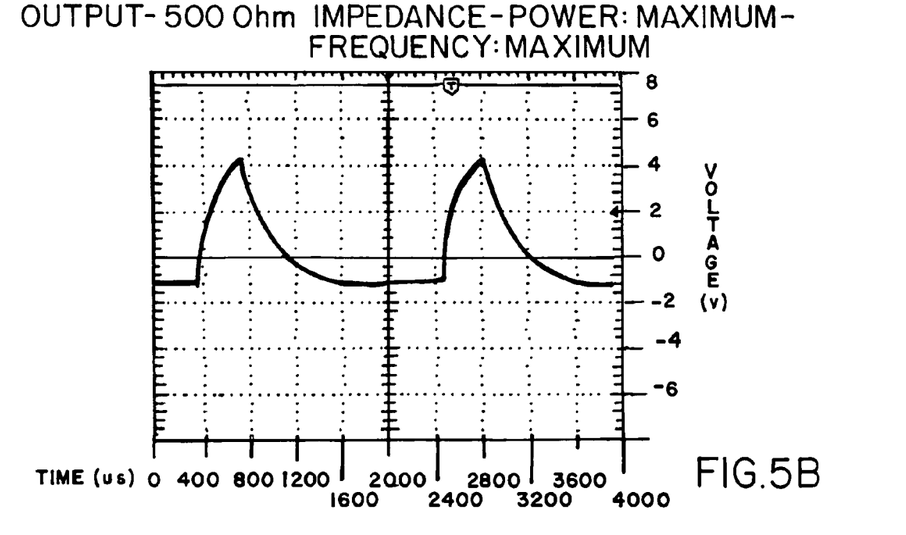
Figure 5C:
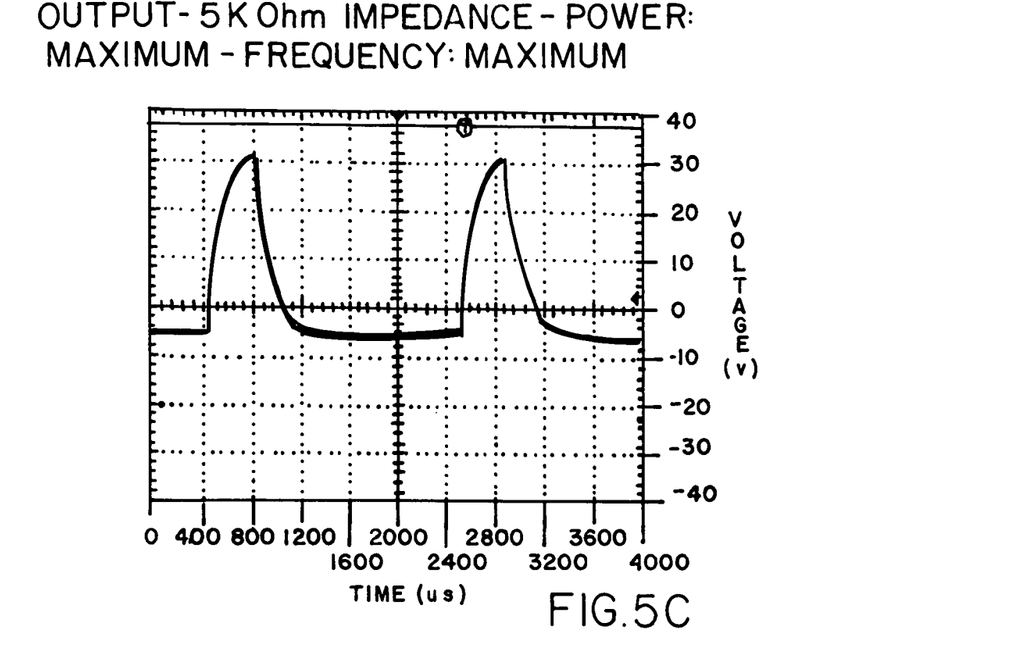
Figure 5D:
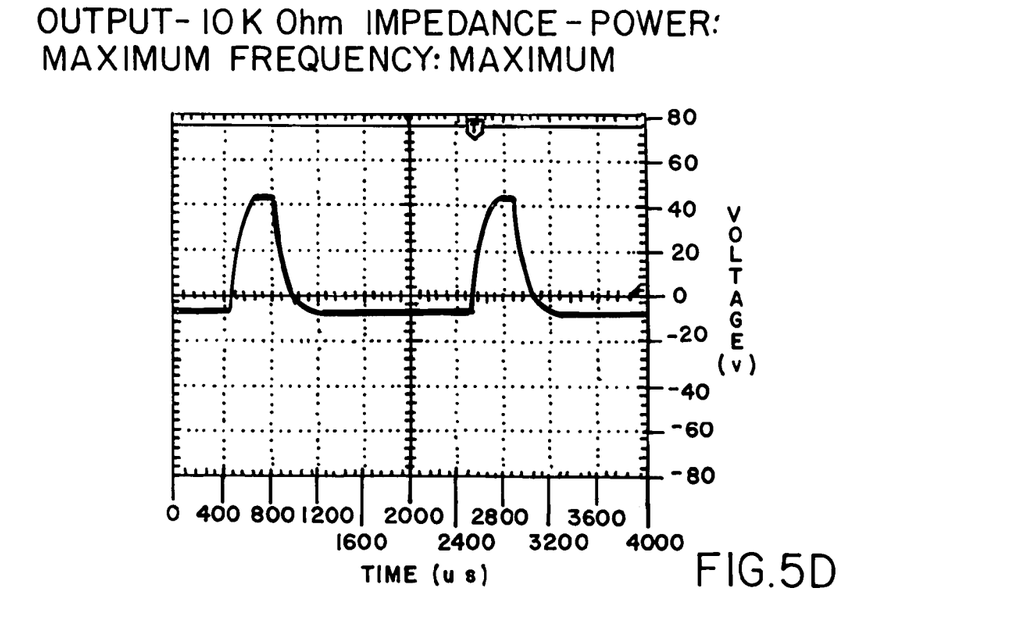

Output waveforms of PTU 108, showing various impedance, power, and frequency relationships are shown in FIGS. 5A-5D. More particularly, FIG. 5A indicates a 1 M-Ohm maximum impedance, in which the output waveform varies depending on the load as shown in FIGS. 5B-5D. That is, FIG. 5B shows voltage versus time at 500 ohms. FIG. 5C shows voltage versus time at 5000 ohms, and FIG. 5D shows voltage versus time at 10,000 ohms. Therein, changes in load affect both pulse duration and maximum pulse frequency. Maximum pulse frequency lies in a range of 490±6% from 500 ohms to 1,000,000 ohms. Lower impedances have lower maximum pulse rates. Pulse width is fixed at a given impedance, and declines from 0.74 milliseconds at 500 ohms to 0.34 milliseconds at 1,000,000 ohms.

Figure 6:
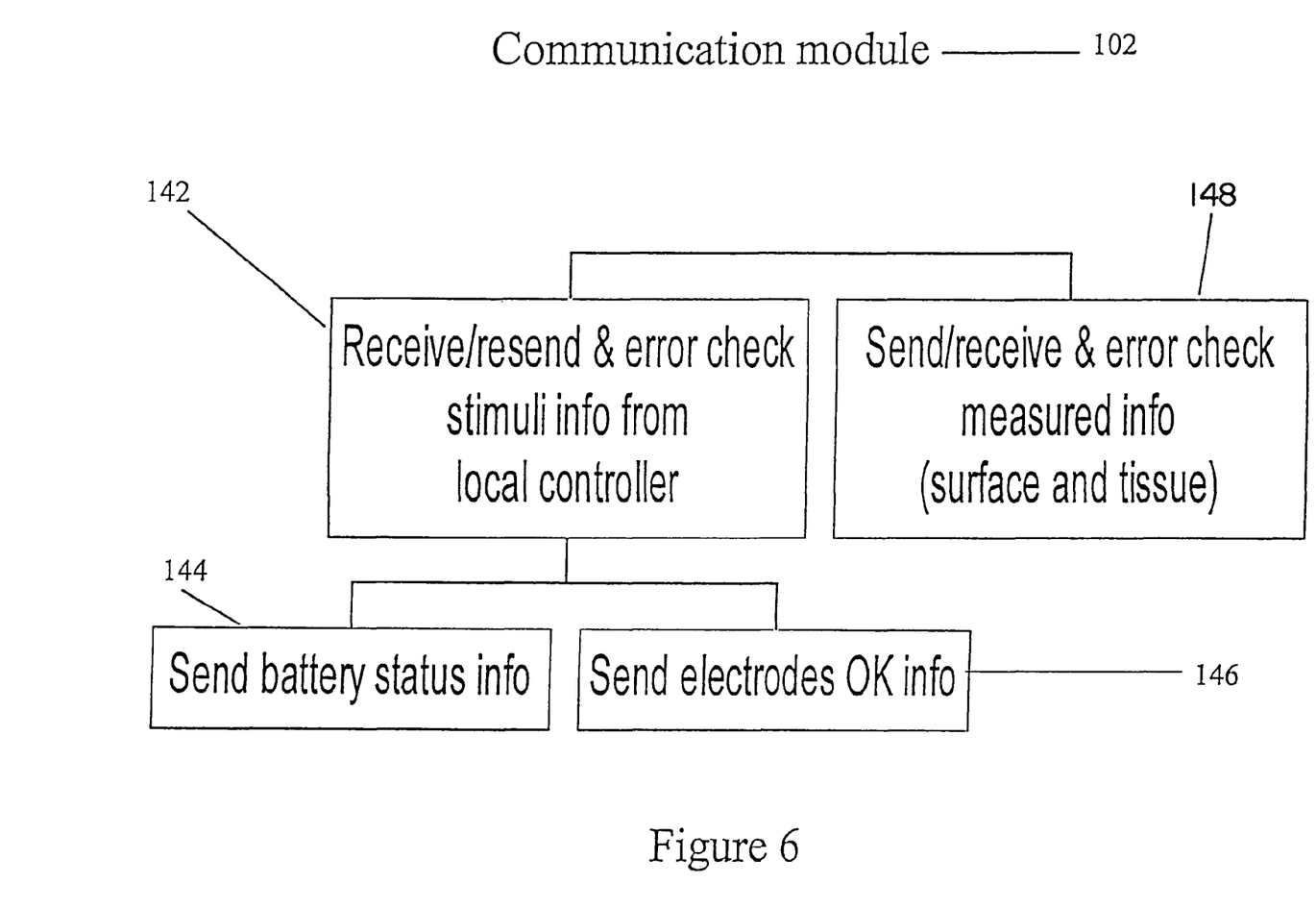
FIG. 6 is a block diagram view of a communication module.

In FIG. 6 is shown communication module 102 and its important internal functions which include subsystem 142 which indicates the receipt and resending of error check stimuli information from a local controller (LC) which includes battery status information 144 and electrode or induction coil status information 146. Communication module 102 also includes subsystem 148 which sends, receives and error checks measurements of both surface and tissue as above described with reference to FIG. 5. Therein the skin-electrode or induction coil and tissue electrode or induction coil impedance is continually monitored at the LC in visual and/or audio terms to thereby enable the medical technician to adjust the pressure of the electrodes or the medium (such as electro-jelly) used between the electrode and the treated tissue.

Figure 7:
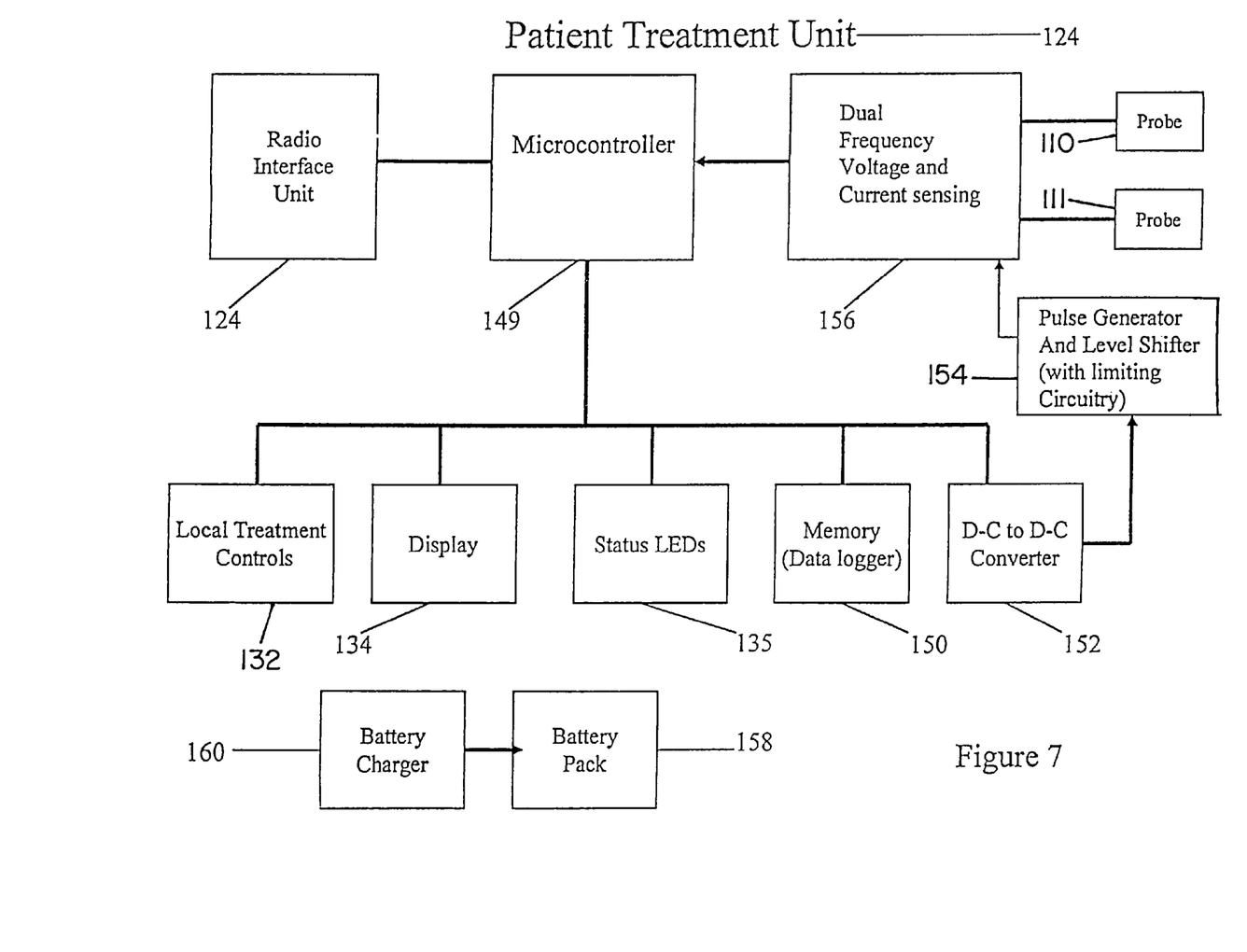
FIG. 7 is a block diagram view of the PTU inclusive of the PC radio interface and local controls of the PTU.

In FIG. 7 are shown the primary constituent subsystems of the PTU 108, these including a microcontroller 149 having a said local treatment controls 132, said display 134, status LEDs 135, a memory 150 used for purposes of recording data, and a DC to DC converter 152. As may be noted, the output of converter 152 feeds into pulse generator and level shifting means 154 which include current and voltage limiting means. The output of said means 154 is provided to means 156 for the simultaneous sensing of voltage and current associated with skin and tissue measurements. The output thereof is provided to said microcontroller 149 which operates with PC 112 through radio interface unit 124. The PTU 108 also includes a battery pack 158 and its charger 160.

Inputs to probes or induction coils 110 and 111 are provided through said dual voltage and current sensing means 156. It is noted that there are two areas in which magnetic resonance fluxuation is measured. The first is through an induction coil and the second is through the treatment measurement probes. The more phase shift (disorder or electrons loss of energy etc) the lower the measured amplitude and the greater the electromagnetic fluxuation.

Figure 8:
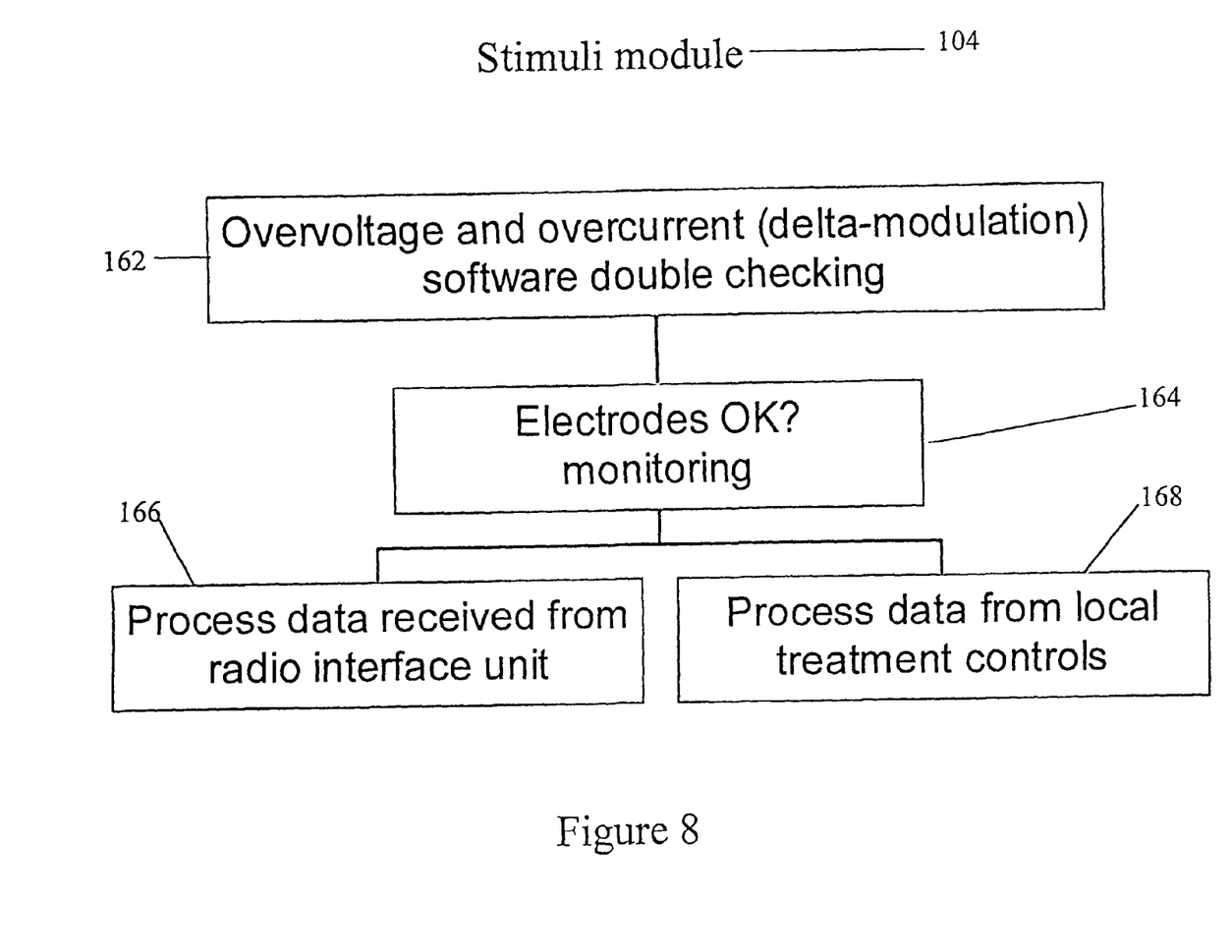
FIG. 8 is a block diagram view of the stimuli module.
Figure 9:
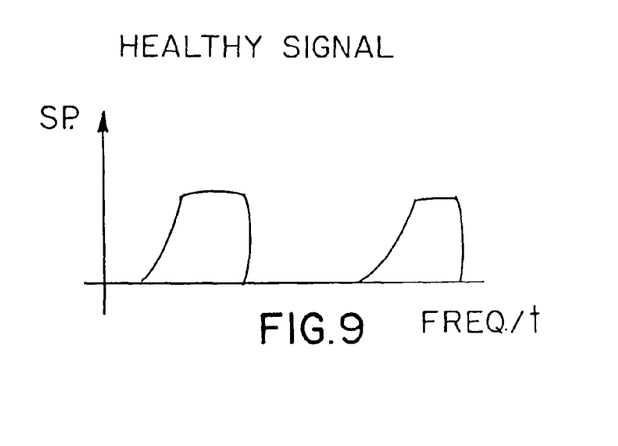
FIGS. 9 and 10 are a respective signal and resonance peak waveforms of a healthy tissue.
Figure 10:
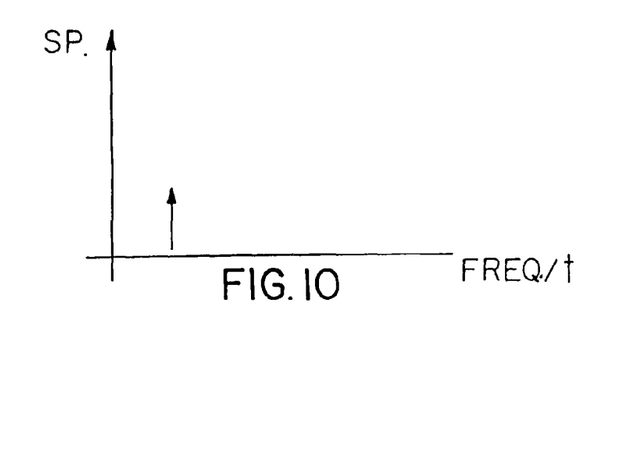

In FIG. 8 is shown stimuli module 104 and, more particularly, over voltage and over-current software monitoring means 162, associated electrode or induction coil monitoring means 164, and associated RI means 166 for processing data received from radio interface unit 124, and means 168 for processing data from local treatment controls 132.

It is to be appreciated that electrodes associated with probes 110/111 and pad 116, that is two electrodes connected via wire, one of which electrodes is provide with a linear potentiometer are used to adjust or select the intensity of the energy provided to the treated tissue. A number of safety features are incorporated into the instant system including visual and/or audio warning means, amplitude limit means (per block 156), amplitude override means, amplitude ramp back means, and patient control means. Therein data transmitted from functional management unit 100 to the PTU 108 includes stimuli frequency, stimuli duty cycle, and patient pain threshold information (based upon patient history) to thereby optimize PTU-side intensity settings. Data transmitted between the PTU and FMU include skin voltage, electromagnetic fluxuation and current (see FIG. 5), phase between skin and voltage current, tissue voltage and current, phase between tissue voltage, electromagnetic fluxuation and current, and stimulus on/off status (see FIG. 3).

Importantly, the local controller (see FIG. 4) of the present EMR system employs various algorithms.

Perhaps most importantly, the LC of the EMR system employs various algorithms, starting with a so called inverse wave form of the injury tissue as a first order basis of treatment, this to be followed by robust stochastic models to generate appropriate stimuli profiles to enable the FMU 100 to provide a sophisticated treatment or correction signal. Therein at least three models or algorithms are contemplated, these including the following:

- sequential, adaptive self-learning method and implementation (for a single electrode pair);
- block adaptive self-learning method and implementation (for an electrode array);
- one and multi dimensional neural network-based controller algorithms;
- sequential data autoregressive method and implementation (for a single electrode pair); and
- block data autoregressive method and implementation (for an electrode array)

In addition, the filtering of the measurement module of the FMU eliminates error signals which typically appear as waveform ripples, to thereby enable generation of a correction or treatment signal from a self-learning multi-electrode PTU, thereby having enhanced efficacy in the cancellation of pain and, ultimately, long term treatment of the condition of interest.

Combinations of algorithms may be employed to generate interchannel waveform correlations to ensure convergence of the model analysis and promotion of its learning curve for the modeling of the tissue injury, treatment profiles and peak resonances associated therewith.

In summary, the technology employ a frequency of 1 Hertz to 1 G hertz, and low gauss (0.1 to 4 Tesla) in treatment signals to increase, decrease, flatten or nullify out of phase resonance peaks of a measured waveform of the tissue to be treated. Similarly, the correction or treatment signal which is applied to treat the abnormal tissue signal obtained by the measurement module is intelligently developed by a self-learning multi-electrode PTU in which various heuristic algorithms are used to ensure convergence and efficient development of models necessary to optimize tissue profile, peak resonance codes, and the use of this information for effective therapy in an array of medical conditions.

This technology also enables treatment of conditions such as arthritis, post surgical pain, post surgical reduction of swelling inflammation and bruising, Osgood Schlater Disease, treatment of organ transplant patients for the purpose of reducing organ rejection, adhesive capsilitus, MS, ALS, motor neuron disease, reduction of keloid scaring treatment of skin graft sites for better vasculasation and better chance of successful graft improvement of circulation and oxygen saturation in compromised tissue and limbs, limb and digit reattachment for better chance of successful graft, improvement and normalization of conductivity in infarcted cardiac tissue, joint inflammation and injuries, fibromyglia, reflex sympathetic dystrophy, neuralgia, peripheral neuropathy, macular degeneration, wounds and sclerdemia. However, a library of tissue profiles and peak resonance codes may be employed in the system in the development of a separate library of profiles and EMR resonance codes for each patient and, also, as a baseline/or electromagnetic structures, of healthy tissue of many types, which might be employed in the generation of an inverse waveform (see discussion in FIGS. 13-14 below) or treatment purposes. Accordingly, my historic library of tissue profiles and peak resonance codes may be intergraded into the stochastic models, as set forth above, to generate appropriate stimuli profiles to enable a sophisticated treatment or correction signal. Therein a simple low-order low pass filtering process, to eliminate signal ripples, constitutes a starting point.

Figure 11:
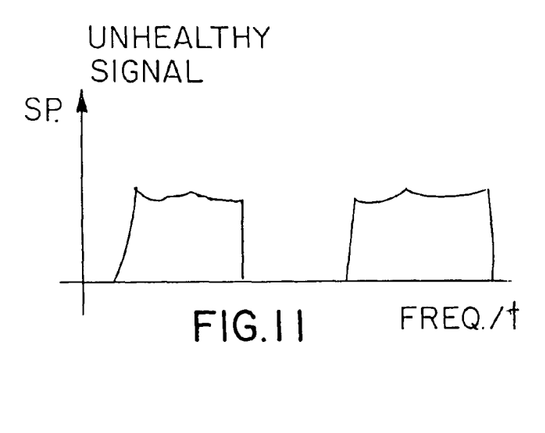
FIGS. 11 and 12 are respective signal and spectrum waveforms of an abnormal tissue.
Figure 12:
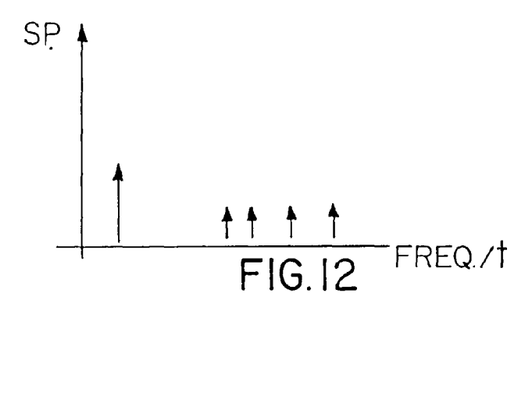
Figure 13:
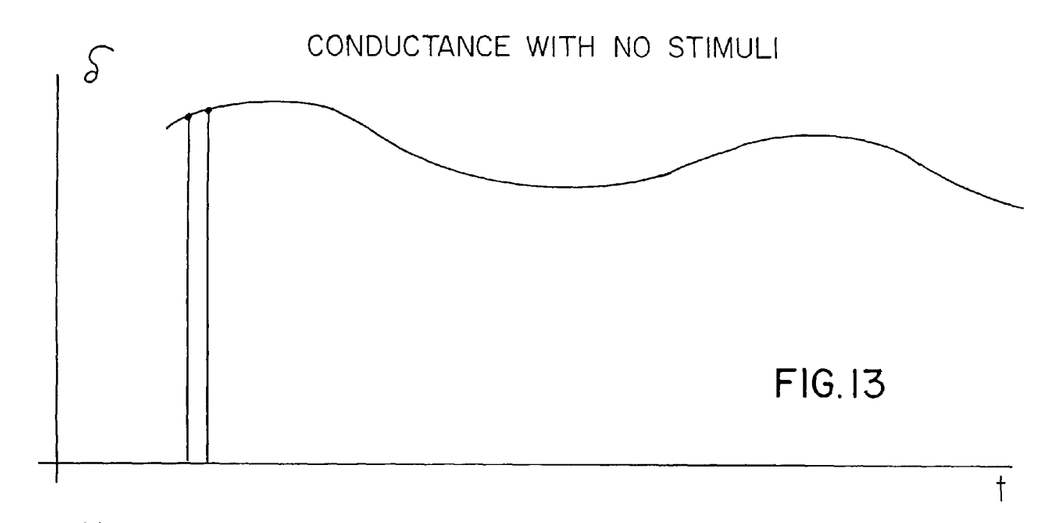
FIGS. 13 and 14 are respective signal and EMR peak for spectra diagrams showing the treatment wave superimposed upon the waveform to be treated.
Figure 14:
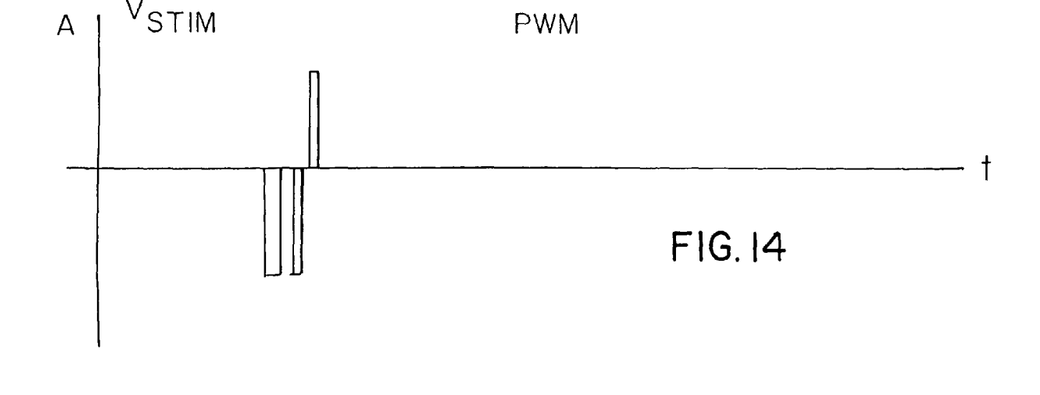

The next step is typically the generation of the inverse waveform or inverse EMR spectra which is a generation of an opposite magnetic single pattern from that shown in FIGS. 11 and 12. The application of this inverse pattern, has a pulse width modulation (PWM) process imposed upon a "sick" signal of the abnormal tissue is shown in FIG. 13. Thereby the system generates and applies to such tissue, a waveform of EMR peak spectra substantially inverse to that of out-of-phase resonances of said tissue signal to thereby increase or nullify EMR peaks of the signal associated with abnormalities. See FIG. 14.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

I claim:

1. A method of analyzing and treating abnormality of human or animal tissues, comprising the steps of:
   outputting by a pulse generator circuit a sequence of electrical pulses at a pulse frequency, the electrical pulses having a pulse width, the pulse generator circuit including current and voltage limiting means;
   the pulse generator controlling the pulse frequency and the pulse width of the electrical pulses, wherein the pulse width is not less than 0.34 milliseconds and is not greater than 0.74 milliseconds, wherein the maximum current output of the pulse generator circuit is not greater than 8.9 milliamps, wherein the maximum charge of electrical pulse does not exceed 7 micro-coulombs, and wherein the pulse frequency does not exceed 1 GHz when treating a pain condition of a patient;
   contacting a body of the patient by a pair of probes that are electrically coupled to the pulse generator via respective electrodes separately connected to the patient treatment unit by respective first and second wires, wherein the electrical pulses are substantially rectangular pulses when the probes have an open circuit between them, wherein one of the probes includes a potentiometer for adjusting a characteristic of the electrical pulses;
   sensing, using a voltage and current sensing circuit, a voltage or a current via the probes when contacting the body of the patient, wherein a peak voltage of the electrical pulses across the probes when a 500 ohm resistance is present across the probes does not exceed 4 volts; and
   detecting an overvoltage or an overcurrent in the electrical pulses.

2. The method of claim 1, wherein the first probe or the second probe includes an induction coil or both the first and second probes each includes a corresponding induction coil.

3. The method of claim 1, wherein a peak voltage of the electrical pulses across the probes when a 5 kilo-ohm resistance is present across the probes does not exceed 30 volts.

4. The method of claim 1, wherein a peak voltage of the electrical pulses across the probes when a 10 kilo-ohm resistance is present across the probes does not exceed 40 volts.

5. The method of claim 1, further comprising indicating an impedance of the skin of the body of the patient as the pulse generator circuit is outputting the electrical pulses to the pair of probes.

6. The method of claim 1, further comprising displaying color changes corresponding to reactive and normal areas of the body under treatment.

7. The method of claim 6, further comprising overlaying a two or three dimensional diagnostic image over the areas of the body under treatment.

8. The method of claim 6, wherein one of the probes includes a wireless induction coil.

9. The method of claim 1, wherein the sensing is carried out simultaneously with the outputting the sequence of electrical pulses.

\* \* \* \* \*